United States Patent
Liddicoat et al.

(10) Patent No.: US 6,769,434 B2
(45) Date of Patent: Aug. 3, 2004

(54) METHOD AND APPARATUS FOR PERFORMING A PROCEDURE ON A CARDIAC VALVE

(75) Inventors: John R. Liddicoat, Sewickley, PA (US); Gregory H. Lambrecht, Natick, MA (US); Todd F. Davenport, Andover, MA (US); William E. Cohn, Chestnut Hill, MA (US); Steven B. Woolfson, Boston, MA (US); Daniel C. Taylor, Brighton, MA (US)

(73) Assignee: Viacor, Inc., Wilmington, MA (US)

( * ) Notice: Subject to any disclaimer, the term of this patent is extended or adjusted under 35 U.S.C. 154(b) by 0 days.

(21) Appl. No.: 09/896,259

(22) Filed: Jun. 29, 2001

(65) Prior Publication Data

US 2002/0042651 A1 Apr. 11, 2002

Related U.S. Application Data

(60) Provisional application No. 60/215,245, filed on Jun. 30, 2000.

(51) Int. Cl.[7] ............................................... A61B 19/00
(52) U.S. Cl. ....................... 128/898; 623/2.11; 623/902
(58) Field of Search ................................ 623/2.11, 902; 128/898; 606/108; 600/16, 37

(56) References Cited

U.S. PATENT DOCUMENTS

| 5,041,130 A | | 8/1991 | Cosgrove et al. |
| 5,716,370 A | * | 2/1998 | Williamson et al. ........ 606/153 |
| 5,972,030 A | | 10/1999 | Garrison et al. |
| 6,010,531 A | * | 1/2000 | Donlon et al. ............... 623/2.1 |

* cited by examiner

Primary Examiner—David J. Isabella
Assistant Examiner—Urmi Chattopadhyay
(74) Attorney, Agent, or Firm—Pandiscio & Pandiscio, P.C.

(57) ABSTRACT

A method for deploying an aortic valve prosthesis includes the steps of: making a first opening leading to the left atrium; passing the valve prosthesis through the opening and into a cardiac chamber of the left side of the heart using a first manipulation instrument; making a second opening in the arterial system and advancing one end of a second manipulation instrument through the arterial opening and into the cardiac chamber; securing the second manipulation instrument to the valve prosthesis; and using the second manipulation instrument to retract at least a portion of the valve prosthesis out of the cardiac chamber.

15 Claims, 16 Drawing Sheets

METHOD AND APPARATUS FOR PERFORMING A PROCEDURE ON A CARDIAC VALVE

REFERENCE TO PENDING PRIOR PATENT APPLICATION

This patent application claims benefit of pending prior U.S. Provisional Patent Application Ser. No. 60/215,245, filed Jun. 30, 2000 for CARDIAC VALVE PROCEDURE METHODS AND DEVICES, which patent application is hereby incorporated herein by reference.

BACKGROUND OF THE INVENTION

Of all valvular heart lesions, aortic stenosis carries the worst prognosis. Within one year of diagnosis, approximately half of all patients with critical aortic stenosis have died, and by three years, this figure rises to approximately 80%. Currently, the most prominent and effective treatment for patients with aortic stenosis is aortic valve replacement via open heart surgery. Unfortunately, this procedure is a substantial and invasive undertaking for the patient.

While there have been significant advances in heart valve technology over the past 30 years, there has been little progress in the development of safer and less invasive valve delivery systems. Aortic valve replacement currently requires a sternotomy or thoracotomy, use of cardiopulmonary bypass to arrest the heart and lungs, and a large incision on the aorta. The native valve is resected through this incision and then a prosthetic valve is sutured to the inner surface of the aorta with a multitude of sutures passing only partly into the wall of the aorta. Given the current invasiveness of this procedure and the requirement to utilize cardiopulmonary bypass, aortic valve replacement surgery is associated with a high risk of morbidity and mortality. This is especially true in elderly patients, and in those patients who require concomitant coronary artery bypass grafting. Even when a good surgical result is achieved, virtually all patients require approximately 6 weeks to several months to fully recover from the procedure. In order to decrease these associated risks of aortic valve surgery, many have pursued novel approaches and technologies.

Less invasive approaches to aortic valve surgery have generally followed two paths.

In the 1980's, there was a flurry of interest in percutaneous balloon valvotomy. In this procedure, a cardiologist introduced a catheter through the femoral artery to dilate the patient's aortic valve, thereby relieving the stenosis. Using the technology available at that time, success was limited: the valve area was increased only minimally, and nearly all patients had restenosis within one year.

More recently, surgeons have approached the aortic valve via smaller chest wall incisions. However, these approaches still require cardiopulmonary bypass and cardiac arrest, which themselves entail significant morbidity and a prolonged post-operative recovery.

The ideal minimally invasive approach to the treatment of aortic valve disease requires aortic valve replacement without cardiopulmonary bypass and without cardiac arrest. Such an approach would greatly reduce patient morbidity and mortality and hasten recovery. Unfortunately, although there has been great progress in the treatment of coronary artery disease without cardiopulmonary bypass (e.g., angioplasty, with or without stenting, and "off-pump" coronary artery bypass grafting), similar advances have not yet been realized in heart valve surgery. With an aging population and improved access to advanced diagnostic testing, the incidence and accurate diagnosis of aortic stenosis will continue to increase. The development of a system for "off-pump" aortic valve replacement would be of significant benefit to this increasing patient population.

There are three important challenges to replacing a diseased aortic valve without cardiopulmonary bypass.

The first challenge is to remove the diseased valve without causing stroke or other ischemic events that might result from the liberation of particulate material while removing the diseased valve.

The second challenge is to prevent cardiac failure during removal of the diseased valve. In this respect it must be appreciated that the aortic valve continues to serve a critical function even when it is diseased. However, as the diseased valve is removed, it becomes acutely and severely incompetent, causing the patient to develop heart failure which results in death unless the function of the valve is taken over by another means.

The third challenge is placing a prosthetic valve into the vascular system and affixing it to the wall of the aorta. More particularly, during cardiac rhythm, the aortic and arterial pressures are substantially greater than atmospheric pressure. Therefore, any sizable incision made to the aorta in order to insert a standard valve prosthesis into the arterial system creates the potential for uncontrollable bleeding from the incision site. Furthermore, even if bleeding is successfully controlled, pressures within the aorta may result in weakening of the aorta caused by aortic wall dissection. In addition, large incisions on the aorta also increase the potential for liberating plaque from the aortic wall that can lead to embolic complications.

For these reasons, prior art valve prostheses potentially suitable for off-pump implantation have relied upon relatively flimsy expandable structures to support and secure the valve within the aorta. More particularly, these prosthetic valves are constructed so that they can be compressed to a relatively small dimension suitable for insertion into the arterial system, advanced to the site of the aortic valve, and then expanded against the aortic wall. Unfortunately, however, none of these relatively flimsy valve prostheses have proven adequate to endure the repetitive stresses undergone by the aortic valve over the ten to twenty years typically required.

In addition to the foregoing, the precise placement of such expandable prosthetic valves in the correct sub-coronary position can be extremely challenging, particularly in view of the high pressure, pulsatile blood flow passing through the aorta. Furthermore, expandable prosthetic valves would typically be positioned from a remote artery, which would reduce the ability to precisely control the placement and positioning of the device and therefore would increases the risk of obstructing the coronary arteries. The expandable prosthetic valves are held on the ends of elongate, flexible catheters that are threaded into the aorta, around the aortic arch and then expanded. The pulsatile flow during cardiac rhythm induces a to-and-fro motion of the valve prosthesis relative to the aorta that makes the timing of valve expansion critical for proper placement of the expandable prosthetic valve and hence the survival of the patient.

Finally, many of the challenges discussed in the foregoing section pertaining to aortic valve replacement are also relevant to other procedures in the aortic root such as aortic valve resection, aortic valve decalcification, stent grafting for aortic dissections, etc.

SUMMARY OF THE INVENTION

It is, therefore, one object of the present invention to enable the passage of a device from the left atrium, through the left ventricle, and into the arterial system.

Further, another object of the present invention is to enable the implantation of a device in the arterial system without cardiopulmonary bypass.

Further, another object of the present invention is to enable the implantation of a prosthetic valve in the arterial system without cardiopulmonary bypass.

Another object of the present invention is to allow the insertion of such a valve while minimizing the risks to the patient posed by large arterial incisions.

And another object of the present invention is to simplify the precise placement of such a valve.

Further, another object of the present invention is to enable the implantation of a device other than a valve, such as but not limited to a valve resection tool, a decalcifying tool, an aortic valve repair tool, or a stented aortic graft, in the arterial system without cardiopulmonary bypass.

Another object of the present invention is to allow the insertion of a device other than a valve, such as but not limited to a valve resection tool, a decalcifying tool, an aortic valve repair tool, or a stented aortic graft, while minimizing the risks to the patient posed by large arterial incisions.

And another object of the present invention is to simplify the precise placement of a device other than a valve, such as but not limited to a valve resection tool, a decalcifying tool, an aortic valve repair tool, or a stented aortic graft.

The present invention relates to a method and apparatus for positioning a device in the arterial system. More specifically, the present invention relates to a method and apparatus for positioning an aortic valve prosthesis in the aorta or aortic outflow tract, with or without cardiopulmonary bypass.

One aspect of the present invention is a method for deploying an aortic valve prosthesis. This valve prosthesis may include any of the known aortic valves including, but not limited to, stented and unstented bioprosthetic valves, stented mechanical valves, and expandable or self-expanding valves, whether biological or artificial.

In one aspect of the invention, there is provided a method of inserting a prosthesis or device from a lower pressure region into a higher pressure region of the cardiovascular system comprising the steps of: making an opening in a wall of a lower pressure region of the cardiovascular system; advancing the prosthesis or device through the opening and into the lower pressure region; and advancing the prosthesis or device through a natural barrier between the lower pressure region and the higher pressure region.

In another aspect of the invention, there is provided a method of inserting a prosthesis or device into a vessel within the arterial system comprising the steps of: making an opening in a wall of a low pressure region of the heart; advancing the prosthesis or device through the opening and into the low pressure region; advancing the prosthesis or device through a natural barrier between the low pressure region and the left ventricle; and advancing the prosthesis or device from the left ventricle into the arterial system and the vessel.

And in another aspect of the invention, there is provided a method of inserting a prosthesis or device into a vessel within the arterial system comprising the steps of: making an opening in a wall of the left atrium; advancing the prosthesis or device through the opening and into the left atrium; advancing the prosthesis or device through the mitral valve and into the left ventricle; and advancing the prosthesis or device from the left ventricle into the arterial system and the vessel.

And in another aspect of the present invention, there is provided a method for positioning a device in the arterial system comprising the steps of: making a first opening leading to the left atrium; passing a valve prosthesis through the first opening and into a cardiac chamber of the left side of the heart using a first manipulation instrument; making a second opening in the arterial system and advancing one end of a second manipulation instrument through the second opening and into the aforementioned cardiac chamber; securing the second manipulation instrument to the valve prosthesis; and then using the second manipulation instrument to retract at least some portion of the valve prosthesis out of the aforementioned cardiac chamber.

An alternative method for positioning a device in the arterial system comprises the steps of: making an opening leading to the left atrium; passing a valve prosthesis through the opening and into a cardiac chamber of the left side of the heart using an articulating manipulation instrument; using the articulating manipulation instrument to guide the valve prosthesis into the arterial cardiac chamber; releasing the valve prosthesis into a desired position: and then retracting at least a portion of the articulating manipulation instrument out of the aforementioned cardiac chamber and left atrium.

The pressure of blood flowing through the left atrium is very low, peaking at a few inches of water during the cardiac cycle. This pressure is a small fraction of that found within the arterial system and thus permits insertion of a conventional valve prosthesis through a relatively large opening formed in the wall of the left atrium without the risk of uncontrollable bleeding. In this respect it will be appreciated that various methods are known to those skilled in the art for controlling bleeding from an incision into the left atrium. The left atrium also rarely suffers from atherosclerotic plaque formation or calcification, thus minimizing the risk of embolic debris during such incision.

Another aspect of the present invention is the use of a prosthesis holding apparatus for releasably holding the valve prosthesis during manipulation to its implant site. The prosthesis holding apparatus may be secured to the prosthetic valve at any suitable location(s) through the use of any of a variety of approaches including, but not limited to, suture loops, barbs, hooks, grasping jaws, opposing magnetic poles, friction fits and the like. The prosthesis holding apparatus is configured to provides first and second manipulation mounts for engagement by the aforementioned first and second manipulation instruments, respectively, whereby the prosthetic valve can be delivered to its implant site. This construction is highly advantageous in that it permits the valve prosthesis to be passed easily and reliably from the first manipulation instrument to the second manipulation instrument within the vascular system.

In an alternative preferred embodiment, the prosthetic holding apparatus is attached on the ventricular side of the prosthesis. The aforementioned first manipulation instrument would articulate at or near the prosthetic valve to facilitate manipulation of the prosthesis holding apparatus (and hence the prosthesis itself) through the smallest possible incision site, then through the left atrium, the mitral valve and within the heart to align and position the prosthesis within the aortic annulus or left ventricular outflow track. In this alternative embodiment, there is no need for the aforementioned second manipulation instrument or the second manipulation mount.

In addition, if the prosthesis holding apparatus is attached on the aortic side of the prosthesis, the manipulation instrument may articulate and may be introduced into the arterial system, brought across the mitral valve into the left atrium, out the left atrium to pick up the prosthesis holding apparatus (and hence the prosthesis) and then retracted back to position the prosthesis directly into the aortic annulus without the need for another manipulation instrument.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like elements and further wherein.

DETAILED DESCRIPTION OF THE PREFERRED EMBODIMENTS

The present invention can be used to implant a variety of prostheses into the arterial system or left side of the heart.

The prosthesis used in the preferred embodiment is an aortic valve prosthesis. Alternatively, the prosthesis may comprise, but is not limited to, a cylindrical arterial stent, an arterial prosthesis or graft, a ventricular assist device, a device for the treatment of heart failure such as an intraventricular counterpulsation balloon, chordae tendinae prostheses, arterial filters suitable for acute or chronic filtration of emboli from the blood stream, arterial occlusion devices and the like.

For clarity of illustration, the present invention will hereinafter be discussed in the context of implanting an aortic valve prosthesis.

It should also be appreciated that the present invention may be practiced either "on-pump" or "off-pump". In other words, the present invention may be performed either with or without the support of cardiopulmonary bypass. The present invention also may be performed either with or without cardiac arrest.

Figure 1:
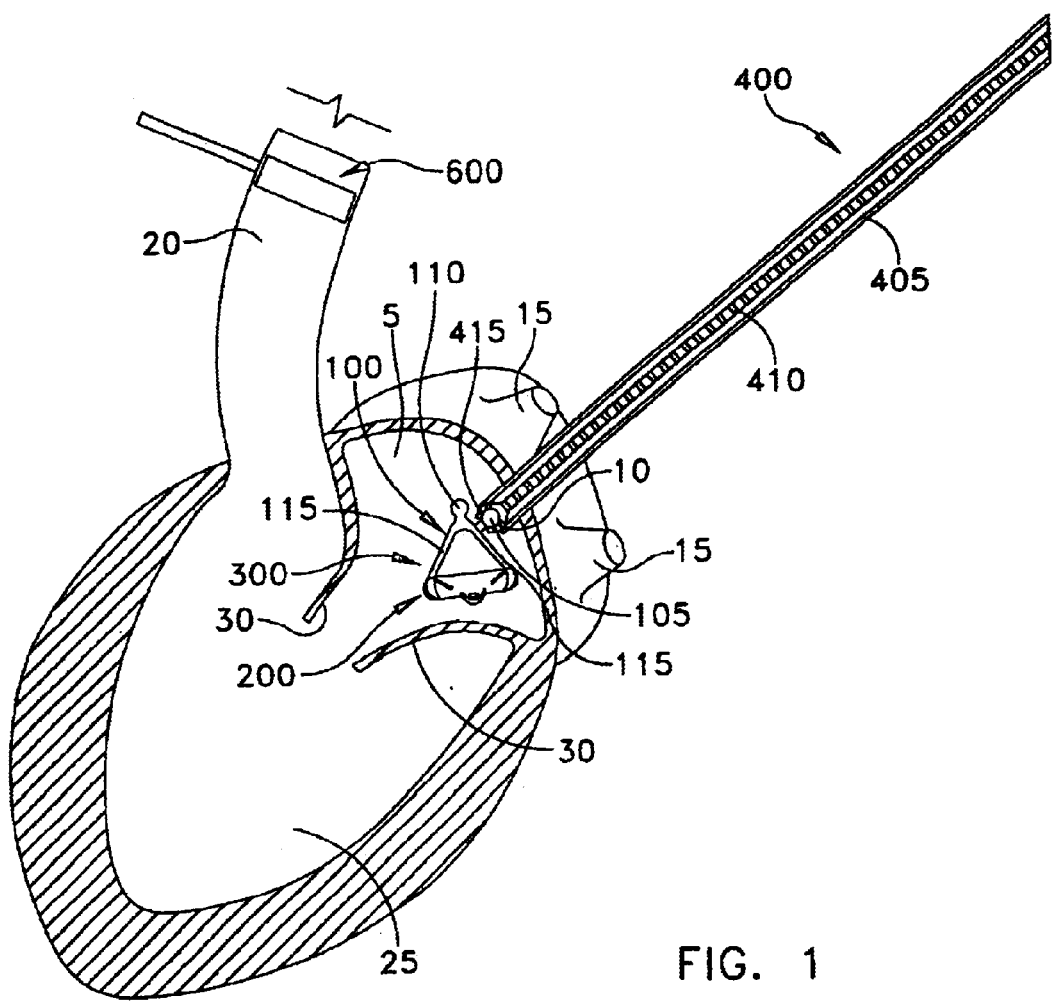
FIG. 1 is a schematic side view showing the introduction of a valve prosthesis and prosthesis holding apparatus into the left atrium of the heart, through an atriotomy, using a first manipulation instrument.

Looking now at FIG. 1, there is shown an exemplary embodiment of the present invention. A prothesis holding apparatus 100 is secured to a prosthetic valve 200 so as to form a temporary prosthetic assembly 300. A first manipulation instrument 400 is secured to a first manipulation mount 105 formed on prosthesis holding apparatus 100, whereby temporary prosthetic assembly 300 may be moved about by first manipulation instrument 400. Temporary prosthetic assembly 300 has been positioned in left atrium 5 by passing first manipulation instrument 400 through atriotomy 10. Alternatively, the temporary prosthetic assembly 300 could be passed into the left atrium 5, using first manipulation instrument 400, through any of the pulmonary veins 15. And in another form of the invention, temporary prosthesis assembly 300 could be passed into the left atrium by first passing the assembly into the right atrium via an atriotomy, and then into the left atrium through an incision made in the interatrial septum.

Prosthetic valve 200 is preferably a conventional mechanical aortic valve of the sort well known in the art, although other forms of valve prostheses may also be used.

In one preferred form of the invention, first manipulation instrument 400 functions by virtue of the relative motion of an outer cannula 405 relative to an inner grasper 410. More particularly, inner grasper 410 has an elastically deformable distal gripper 415 which is open when the gripper is outside of outer cannula 405. However, when deformable gripper 415 is pulled at least partially into or against outer cannula 405, gripper 415 is elastically deformed into a closed position, whereby it may grip an object, e.g., first manipulation mount 105 formed on prosthesis holding apparatus 100. First manipulation instrument 400 is shown in FIG. 1 in its closed position, wherein deformable gripper 415 is closed about first manipulation mount 105, such that prosthesis holding apparatus 100, and hence the entire temporary prosthetic assembly 300, is held secured to the distal end of first manipulation instrument 400.

The specific embodiment of first manipulation instrument 400 shown in FIG. 1 is presented as an illustrative example only, and is not intended to limit the scope of the present invention. Many other arrangements may be used for releasably gripping first manipulation mount 105 formed on prosthesis holding apparatus 100. Furthermore, first manipulation mount 105 may itself have many potential shapes and properties to enable releasable attachment to first manipulation instrument 400. Other possible configurations for releasably securing first manipulation mount 105 to first manipulation instrument 400 include, but are not limited to, opposing magnet poles in the mount and instrument, adhesives, a press fit between mount and instrument, threaded couplings, suture loops, a balloon or balloons expanded within a mating cavity, collapsible barbs, etc. For the purposes of the present invention, the important point is that some arrangement be provided for releasably securing the prosthesis holding apparatus (and hence the prosthetic valve) to a manipulation instrument.

Still looking now at FIG. 1, first manipulation instrument 400 is shown as having a long axis that extends outside of the heart, with first manipulation instrument 400 being straight along that axis. However, it should also be appreciated that first manipulation instrument 400 may, alternatively, be formed with a curve at one or more location along this length. Furthermore, first manipulation instrument 400 may be constructed so as to allow articulation at the distal end, the proximal end, or both, or at any point therebetween. In addition, first manipulation instrument 400 may be formed either entirely rigid or substantially flexible, along all or part of its length.

First manipulation instrument 400 is also shown as having a relatively small dimension perpendicular to its long axis. This configuration allows atriotomy 10 to be reduced in size after the passage of temporary prosthetic assembly 300 into left atrium 5. This perpendicular dimension may be constant or varied along the long axis of first manipulation instrument 400.

The specific embodiment of the prosthesis holding apparatus 100 shown in FIG. 1 is presented as an illustrative example only, and is not intended to limit the scope of the present invention. Many other arrangements may be used for releasably gripping prosthetic valve 200 and for providing first manipulation mount 105, as well as providing a second manipulation mount 110 that will be discussed below. In FIG. 1, first manipulation mount 105 and second manipulation mount 110 are shown as spherical additions to struts 115 extending away from prosthetic valve 200. These spheres are intended to fit, respectively, within the deformable gripper 415 of first installation instrument 400 and a deformable gripper 515 of a second installation instrument 500 (discussed below). First manipulation mount 105 and/or second manipulation mount 110 could, alternatively, be indentations within a portion of male or female threaded extensions from, magnetized surfaces of, slots or holes in or through, prosthesis holding apparatus 100, etc. Furthermore, first manipulation mount 105 and/or second manipulation mount 110 could be portions of the struts 115 extending away from prosthetic valve 200, where those portions may be either reduced or enlarged in dimension relative to neighboring portions of the struts. Many other constructions may also be used to form first manipulation mount 105 and second manipulation mount 110. For the purposes of the present invention, the important point is that some arrangement be provided for releasably securing the prosthesis holding apparatus (and hence the prosthetic valve) to manipulation instruments.

Still looking now at FIG. 1, it will be appreciated that the native aortic valve has been removed. Removal of the native aortic valve is not a necessary element of the present invention, but may be incorporated into the preferred method. Removal of the native aortic valve may be accomplished either before or after passage of the temporary prosthetic assembly 300 into left atrium 5.

When the methods and devices of the present invention are employed during an off-pump valve replacement procedure, it may be beneficial to provide temporary valves and/or filters in the arterial system, downstream of the site of the native aortic valve. Thus, for example, in FIG. 1 there is shown a temporary valve 600 which may be used to support cardiac function during and following removal of the diseased cardiac valve. Temporary valve 600 is shown positioned in aorta 20. Alternatively, temporary valve 600 may be positioned in the aortic arch or the descending aorta. In addition, temporary valve 600 may incorporate a filter therein to mitigate the risks of embolic complications. Alternatively, a separate filter may be employed within the aorta and/or the branch arteries extending therefrom.

Figure 2:
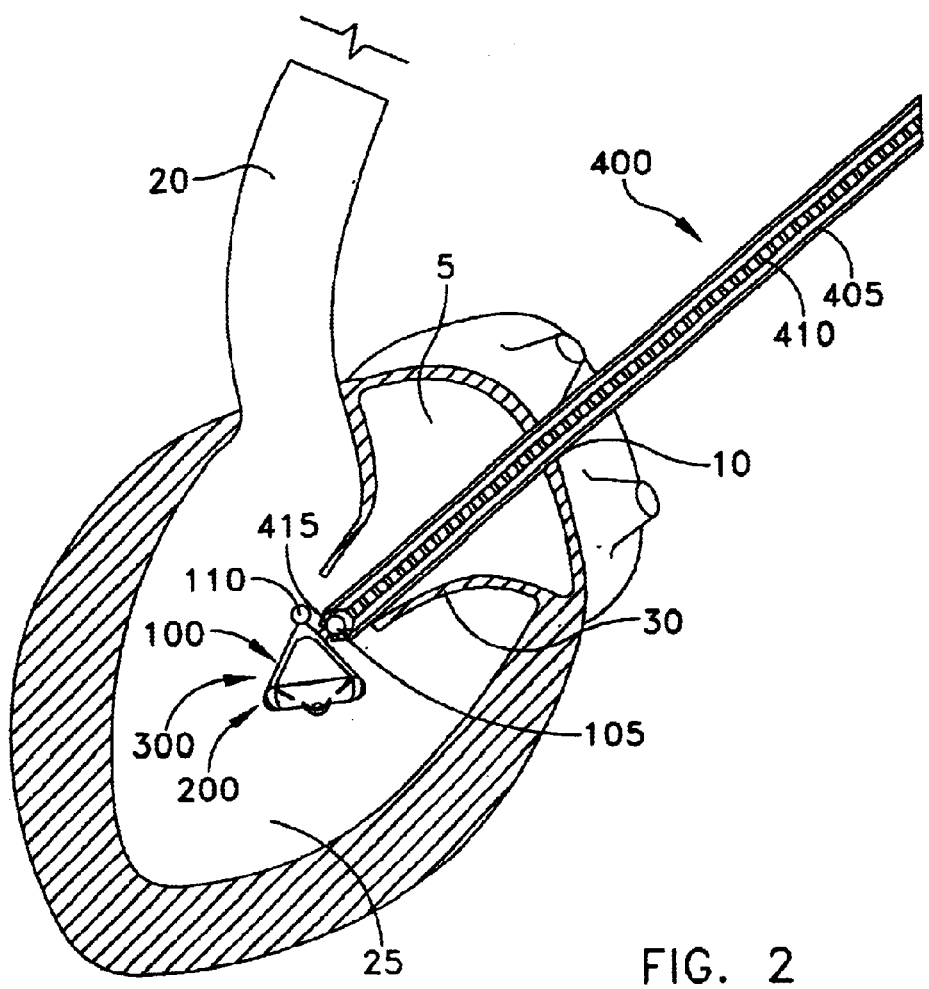
FIG. 2 is a schematic side view showing passage of the apparatus of FIG. 1 from the left atrium, through the mitral valve, and into the left ventricle.

FIG. 2 shows first manipulation instrument 400 being used to manipulate temporary prosthetic assembly 300 (and hence prosthetic valve 200) into left ventricle 25 through mitral valve 30. After temporary prosthetic assembly 300 has passed into left ventrical 25, the first manipulation instrument 400 will continue to traverse mitral valve 30; however, the reduced perpendicular cross-section of first manipulation instrument 400 will cause only minimal disruption of the function of mitral valve 30.

Figure 3:
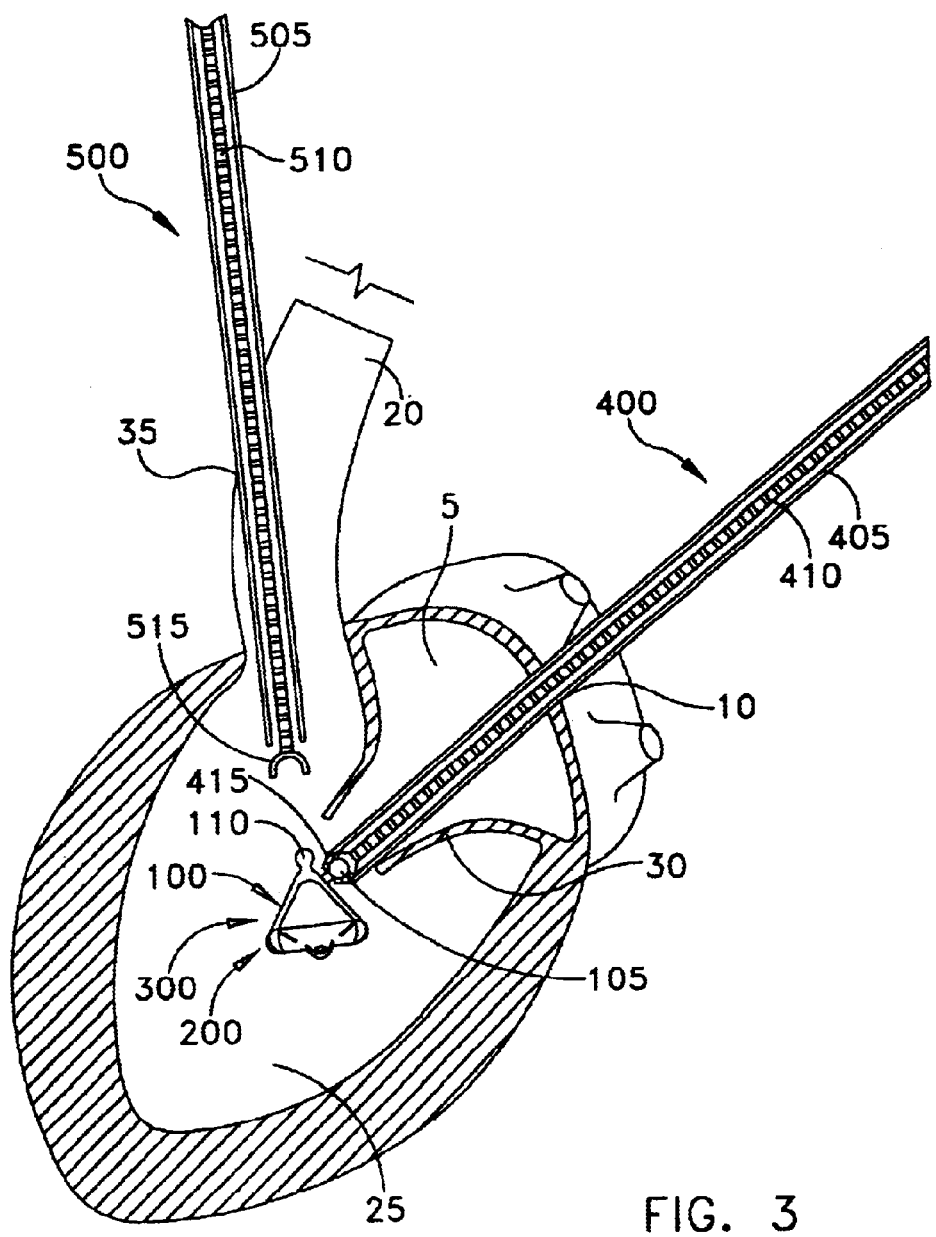
FIG. 3 is a schematic side view showing the introduction of a second manipulation instrument into the left ventricle through an arteriotomy into the arterial system.

FIG. 3 shows the insertion of a second manipulation instrument 500 through the arterial system and into left ventricle 25. Second manipulation instrument 500 is shown being inserted through an incision 35 on aorta 20. Alternatively, second manipulation instrument 500 could be inserted into a central or peripheral artery and than advanced into left ventricle 25. Aortic incision 35 is small relative to the atriotomy 10 formed in left atrium 5.

Bleeding through incision 35 may be readily controlled through a variety of means. These include, but are not limited to, employing a valved or un-valved arterial cannula, a purse-string suture placed around incision 35 and then pulled tight about second manipulation instrument 500, a side-arm graft sewn to aorta 20 that may be constricted about a region of second manipulation instrument 500, the use of a tight fit between a portion of second manipulation instrument 500 and aortic incision 35, etc.

Second manipulation instrument 500 is shown in FIG. 3 as being of the same form and function of first manipulation instrument 400. Again, outer cannula 505 fits around inner grasper 510, and the relative motion between grasper 510 and cannula 505 can be used to deform gripper 515 between open and closed positions. Alternatively, second manipulation instrument 500 may have any of the variety of other forms and functions described above with respect to first manipulation instrument 400. Furthermore, second manipulation instrument 500 is preferably of a smaller dimension perpendicular to its long axis than first manipulation instrument 400 so as to reduce the risks posed by arteriotomy 35.

Figure 4:
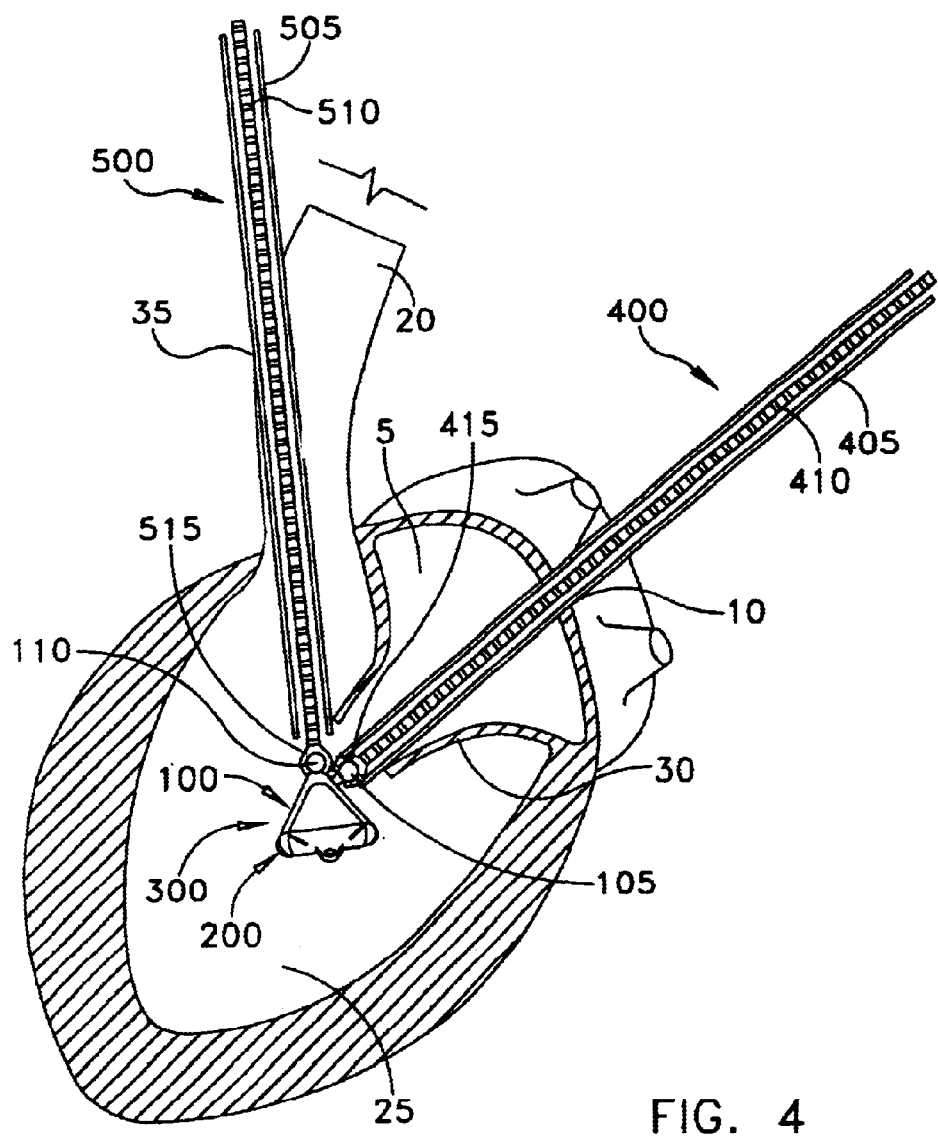
FIG. 4 is a schematic side view showing the second manipulation instrument being attached to the prosthesis holding apparatus while the first manipulation instrument remains secured to the prosthesis holding apparatus.

FIG. 4 shows second manipulation instrument 500 being secured to the second manipulation mount 110 formed on prosthesis holding apparatus 100. This is done while first manipulation instrument 400 is secured to first manipulation mount 105 formed on prosthesis holding apparatus 100, in order that temporary prosthetic assembly 300 will be under control at all times during the "hand-off" between first manipulation instrument 400 and second manipulation instrument 500.

It should be appreciated that the orientation of second manipulation mount 110 is preferably such as to enable the long axis of second manipulation instrument 500 to be substantially perpendicular to the flow area of prosthetic valve 200. This arrangement is particularly helpful when guiding prosthetic valve 200 into its final position within aorta 20 as shown hereafter in FIGS. 6 and 7.

The use of two separate manipulation instruments, and the method of passing valve prosthesis 200 from one to the other, avoids the complex manipulations of valve prosthesis 200 that would be required to position valve 200 within aorta 20 using only a single manipulation instrument introduced through the left atrium. In this respect it should be appreciated that such a "single manipulation instrument" technique has been found to be possible, however, and is best facilitated by using a manipulation instrument capable of bending or articulating at or near the site of its attachment to valve holding apparatus 100. In this respect it has been found that it can be particularly advantageous to provide a manipulation instrument capable of bending or articulating within about 4 cm or so of the point of attachment to valve holding apparatus 100. It has also been found that it can be particularly advantageous for such an articulating instrument to be able to deflect its distal tip by an angle of between about 90 to 180 degrees from the long axis of the first manipulation instrument 400 shown in FIG. 4.

The angular offset of first manipulation mount 105 and second manipulation mount 110 is preferably set to facilitate passage of temporary prosthetic assembly 300 from left atrium 5 to aorta 20 using two substantially straight manipulation instruments, e.g., first manipulation instrument 400 and second manipulation instrument 500. This angle is preferably approximately 45 degrees. However, this angle may also be varied so as to optimize passage of different valve designs or other prostheses using curved, straight or articulating manipulation instruments from various access sites into the left atrium and arterial system. This angle may be fixed or variable on a given prosthesis holding apparatus 100.

Figure 5:
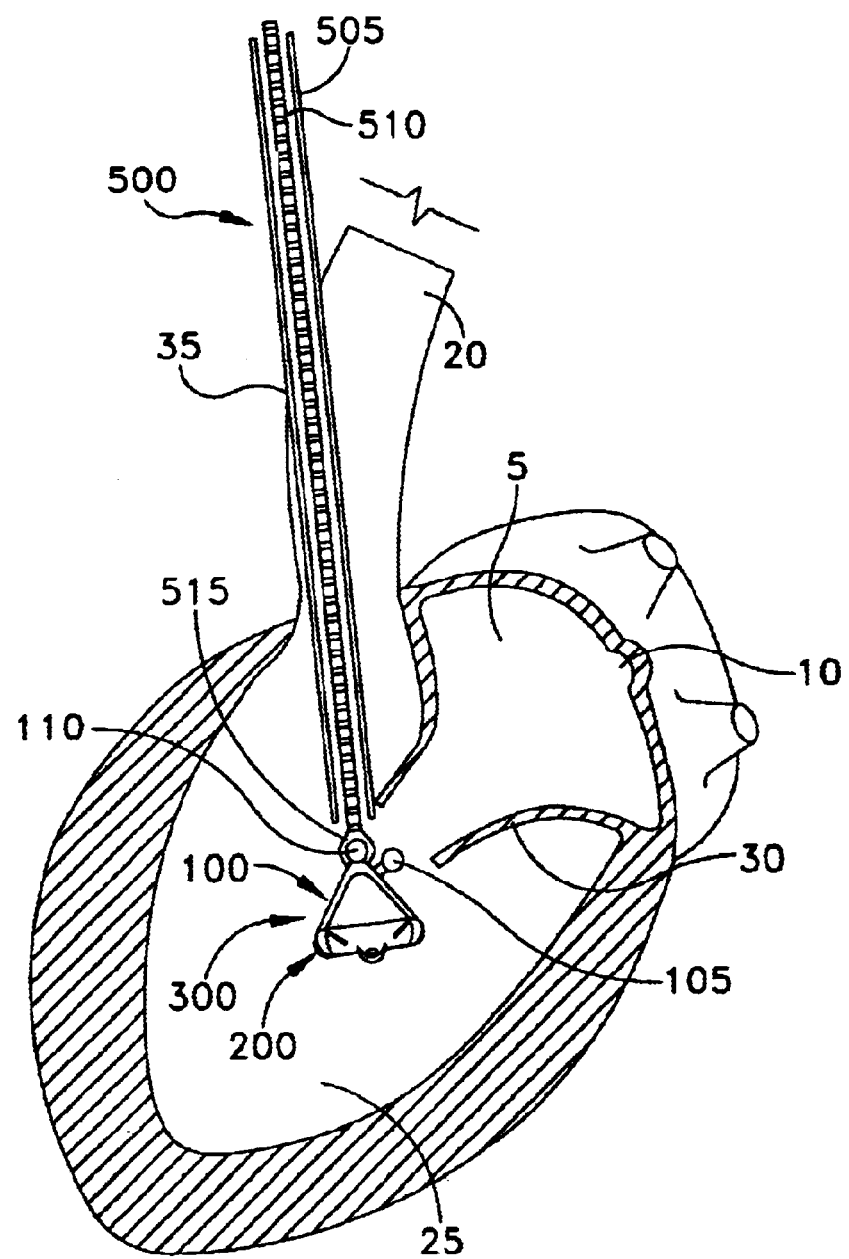
FIG. 5 is a schematic side view similar to that of FIG. 4, except showing the first manipulation instrument being removed from the surgical site while the second manipulation instrument remains secured to the prosthesis holding apparatus.

Once second manipulation instrument 500 is safely secured to second manipulation mount 110, first manipulation instrument 400 may be released from first manipulation mount 105 and removed from left ventricle 5, as shown in FIG. 5. Alternatively, first manipulation instrument 400 may remain secured to prosthesis holding apparatus 100 or prosthetic valve 200 by a flexible tether so as to facilitate re-attachment of first manipulation instrument 400 to valve holding apparatus 100 if necessary.

Figure 6:
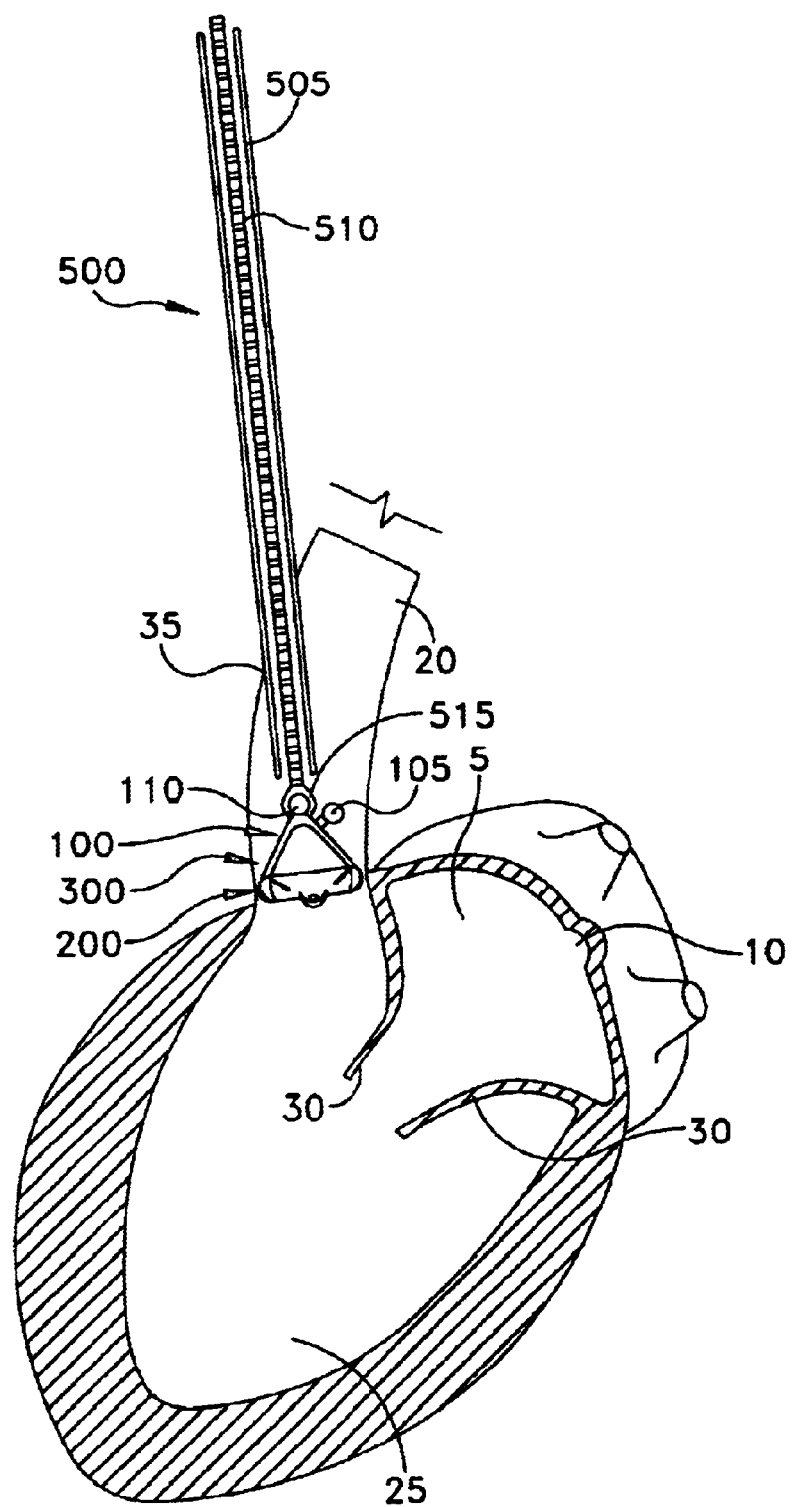
FIG. 6 is a schematic side view showing the second manipulation instrument positioning the prosthetic valve within the aorta prior to fixation.

FIG. 6 shows temporary prosthesis assembly 300 being positioned by second manipulation instrument 500 at a preferred fixation site. This fixation site is preferably upstream of or proximal to the coronary arteries, although this position is not a restrictive requirement of the present invention.

Figure 7:
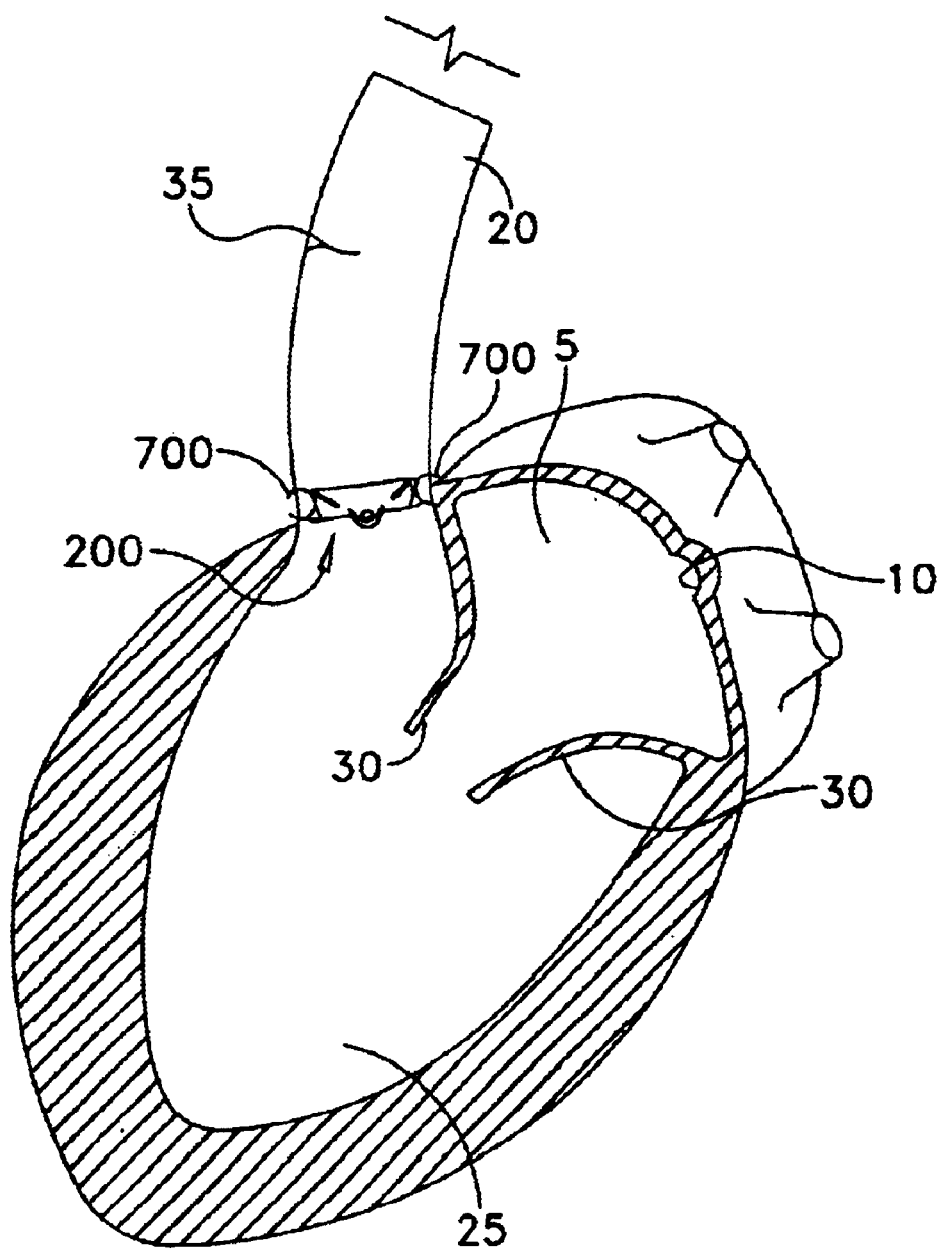
FIG. 7 is a schematic side view showing the prosthetic valve secured to the tissues of the aorta following removal of the second manipulation instrument and prosthesis holding apparatus.

FIG. 7 shows valve prosthesis 200 secured to the walls of aorta 30 and removal of second manipulation instrument 500 and prosthesis holding apparatus 100. In this respect it should be appreciated that prosthesis holding apparatus 100 is preferably wholly or partially flexible, or otherwise collapsible, so as to allow the prosthesis holding apparatus 100 to be collapsed radially and then withdrawn through arteriotomy 35 after prosthesis holding apparatus 100 has been released from prosthetic valve 200. Alternatively, prosthesis holding apparatus 100 may be removed from the vascular system, either partially or entirely, through atriotomy 10 by first manipulation instrument 400, by a tether leading therefrom, or a separate instrument. Of course, in the situation where prosthesis holding apparatus 100 is to be removed via atriotomy 10, the prosthesis holding apparatus 100 should be appropriately mounted to prosthetic valve 200, i.e., prosthesis holding apparatus 100 should be positioned on the atriotomy side of the valve.

In FIG. 7, valve prosthesis 200 is shown secured to aorta 20 using barbs or staples 700. Barbs or staples 700 may be a component of, and/or deployed from, prosthesis holding apparatus 100, and/or valve prosthesis 200, and/or a separate fixation device. Alternatively, barbs or staples 700 may be deployed by a separate instrument inserted through the outer surface of aorta 20, from a remote site in the arterial system, through atriotomy 10 or through some other incision into a cardiac chamber or great vessel.

Figure 8:
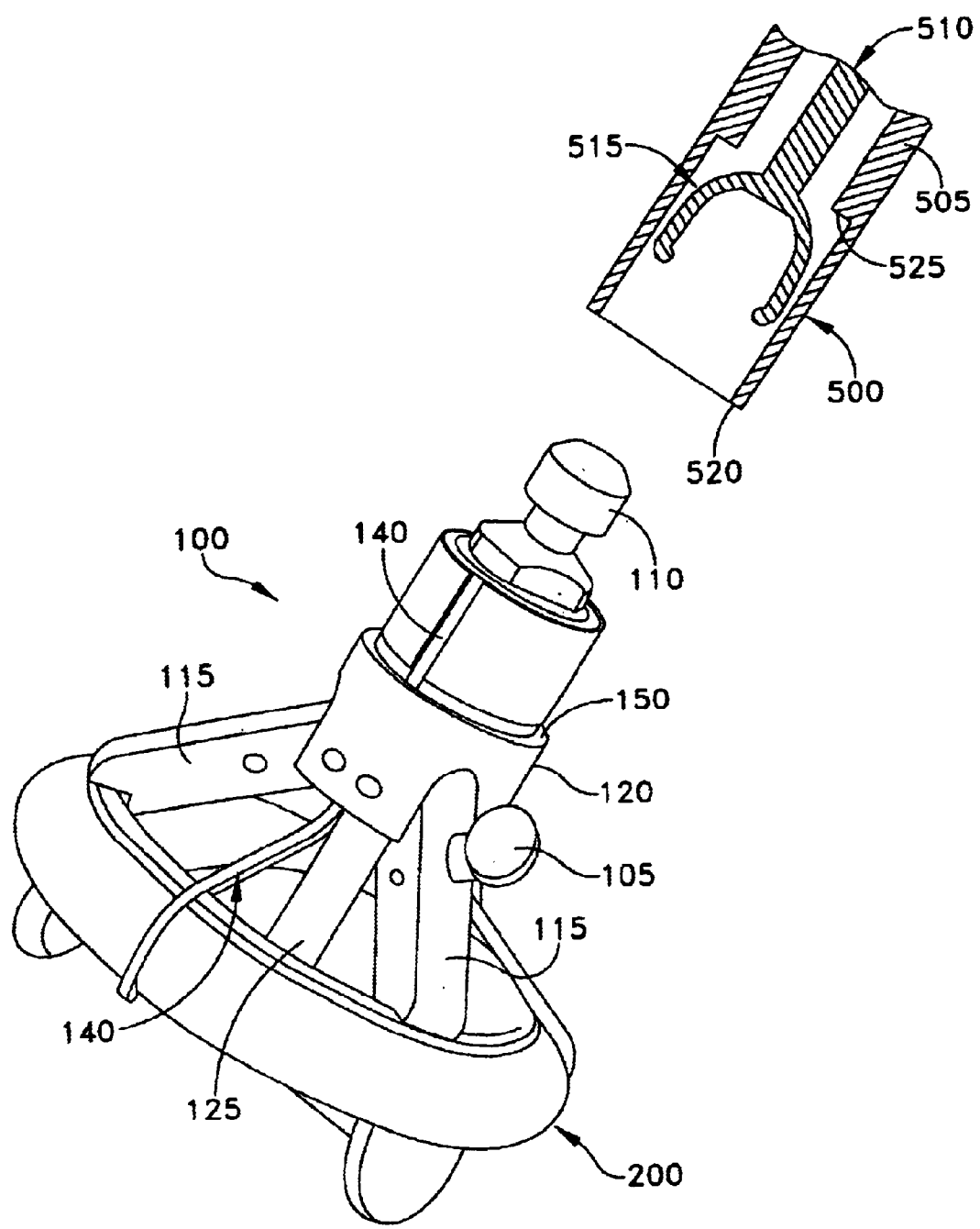
FIGS. 8, 9 and 10 are enlarged schematic views showing a preferred construction for the valve holding apparatus, and for the attachment to, and detachment from, the prosthetic valve.
Figure 9:
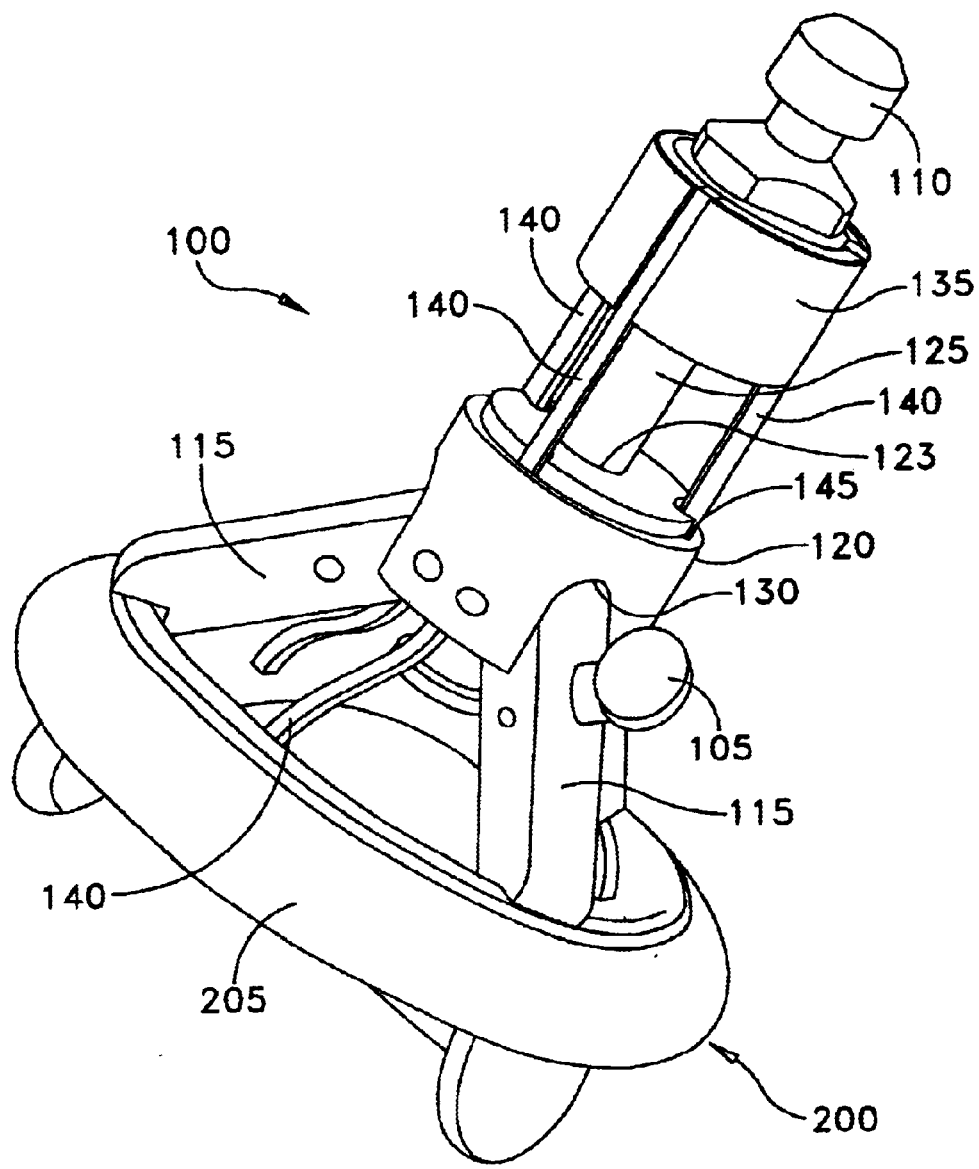
Figure 10:
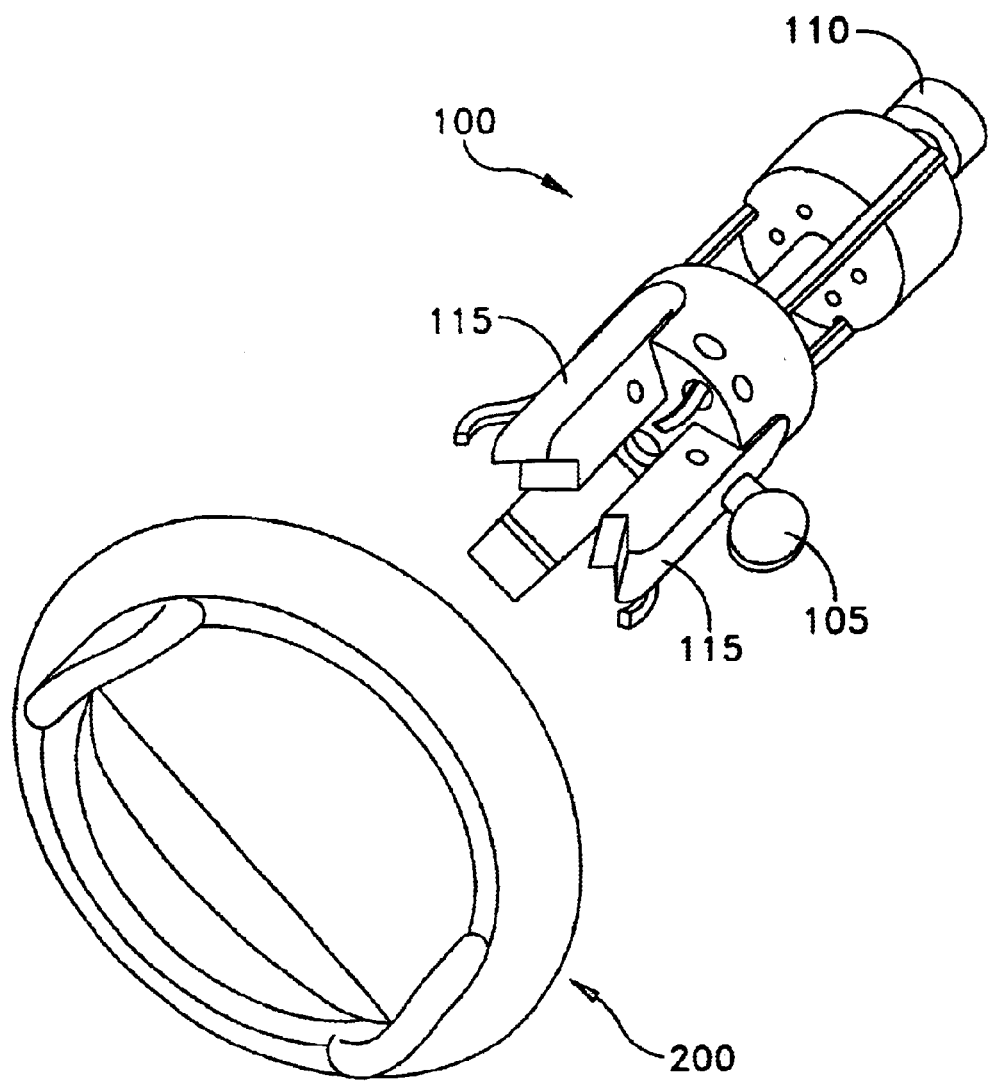

Looking next at FIGS. 8–10, there is shown one preferred configuration for prosthesis holding apparatus 100. More particularly, prosthesis holding apparatus 100 comprises a base 120 having a longitudinal opening 123 (FIG. 9) therein for slidably receiving a rod 125 therethrough. Base 120 also comprises a plurality of side slots 130. Each side slot 130 has a strut 115 pivotally connected thereto. Slots 130 are constructed so that each strut 115 can pivot freely between (i) the position shown in FIGS. 8 and 9, and (ii) the position shown in FIG. 10. A body 135 is mounted on rod 125. A plurality of wire fingers 140 are secured to body 135. Wire fingers 140 extend through holes 145 formed in base 120 and extend around a cuff 205 of prosthetic valve 200. Second manipulation mount 110 is secured to the proximal end of rod 125. First manipulation mount 105 is secured to one of the struts 115. Alternatively, as noted above, first manipulation mount 105 may be formed by a strut 115 itself, provided that first manipulation instrument 400 is appropriately adapted to engage the strut 115 directly.

In use, prosthesis holding apparatus 100 is fit about valve prosthesis 200 so that wire fingers 140 hold valve cuff 205 to struts 115. Prosthesis holding apparatus 100 is then engaged by first manipulation instrument 400, using first manipulation mount 105, and moved into and through left atrium 5, through mitral valve 30 and into left ventricle 25. Then second manipulation tool 500, comprising outer cannula 505 and inner grasper 510 having the deformable gripper 515, engages second manipulation mount 110. A distal tip 520 of outer cannula 505 is placed against edge 150 of base 120 and gripper 515 is drawn proximally within outer cannula 505 until deformable gripper 515 engages shoulder 525, whereupon prosthesis holding apparatus 100 (and hence prosthetic valve 200) will be mounted to second manipulation tool 500. Second manipulation tool 500 is then used to maneuver temporary prosthetic assembly 300 into position, whereupon the valve's cuff 205 is secured to the side wall of the aorta, e.g., with barbs, staples, suture, etc. Then prosthesis holding apparatus 100 is detached from prosthetic valve 200 by pulling inner grasper 510 proximally relative to outer cannula 505 so that wire fingers 140 are pulled past valve cuff 205 (FIG. 9), whereby to free prosthesis holding apparatus 100 from the prosthetic valve 200. Then second manipulation instrument 500 is withdrawn out aorta 20 and arteriotomy 35, with struts 115 folding inwardly (FIG. 10) so as to pass through the arteriotomy. Struts 115 can be adapted to fold inwardly through engagement with the walls of the arteriotomy 35 or, alternatively, additional means (such as springs, cams, etc.) can be provided to fold struts 115 inwardly.

Figure 11:
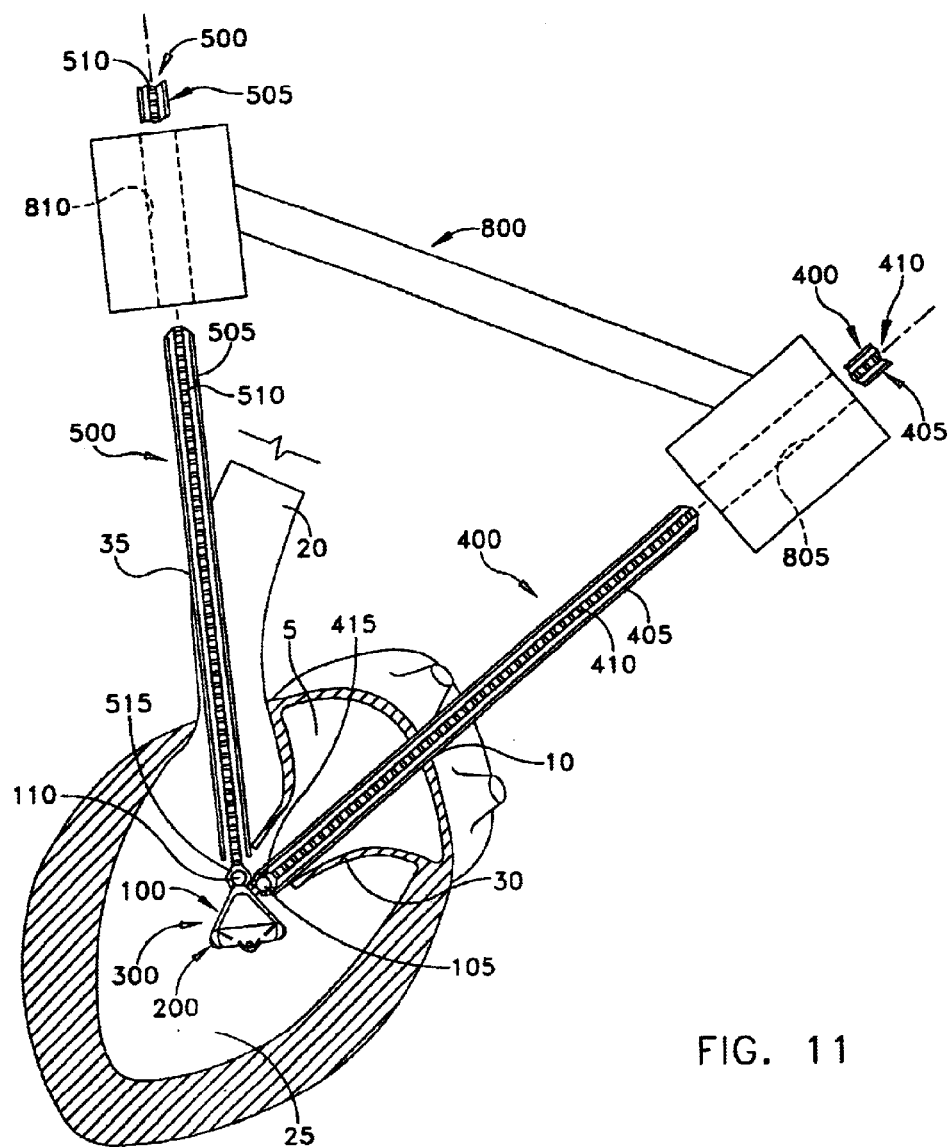
FIG. 11 is a schematic view showing a guide for guiding the second manipulation instrument relative to the first manipulation instrument such that the second manipulation instrument will be aimed directly at the second manipulation mount when the first manipulation mount is secured to the first manipulation instrument.

In practice, it has been found that it can sometimes be difficult to locate second manipulation mount 110 with second manipulation instrument 500 so as to "hand off" temporary prosthesis assembly 300 from first manipulation instrument 400 to second manipulation instrument 500. This can be particularly true where the procedure is to be conducted "off-pump", i.e., without stopping the heart. To this end, and looking now at FIG. 11, there is shown a guide 800 for guiding second manipulation instrument 500 relative to first manipulation instrument 400 such that second manipulation instrument 500 will be aimed directly at second manipulation mount 110 when first manipulation mount 105 is secured to first manipulation instrument 400. More particularly, guide 800 comprises a first passageway 805 for slidably receiving first manipulation instrument 400, and a second passageway 810 for slidably receiving second manipulation instrument 500. Passageways 805 and 810 are oriented so that second manipulation instrument 500 will be aimed directly at second manipulation mount 110 when temporary prosthesis assembly 300 is held by first manipulation instrument 400 engaging first manipulation mount 105.

In accordance with the present invention, it is also possible to enter the left atrium other than through an exterior wall of the left atrium. Thus, for example, it is possible to introduce the prosthetic valve through an opening in an exterior wall of the right atrium, pass the prosthetic valve through an incision in the interatrial septum and across to the left atrium, and then advance the prosthetic valve to its implantation site via the mitral valve and the left ventricle.

As noted above, the manipulation instrument(s) do not need to take the form of the installation instrument 400 or 500. It is also possible to deliver the prosthetic valve to its implant site using a guidewire and a pusher tool riding on the guidewire.

Figure 15:
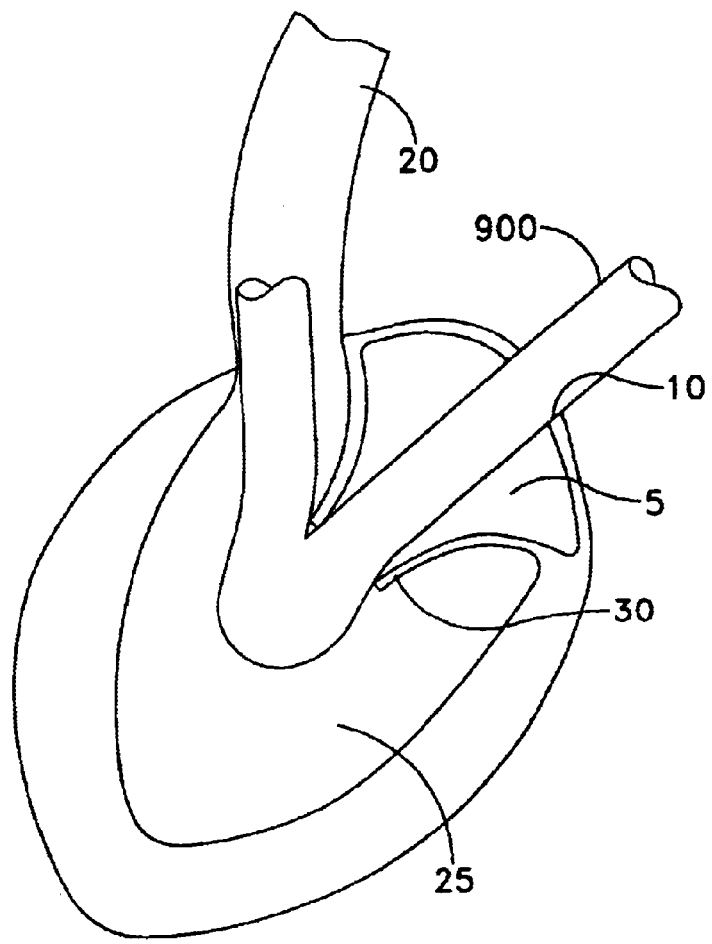
FIG. 15 is a schematic view showing use of a tube through which a prosthesis may be passed into a left atrium, the tube extending through an atrionomy, left atrium, a mitral valve, a left ventricle and into an aorta.
Figure 16:
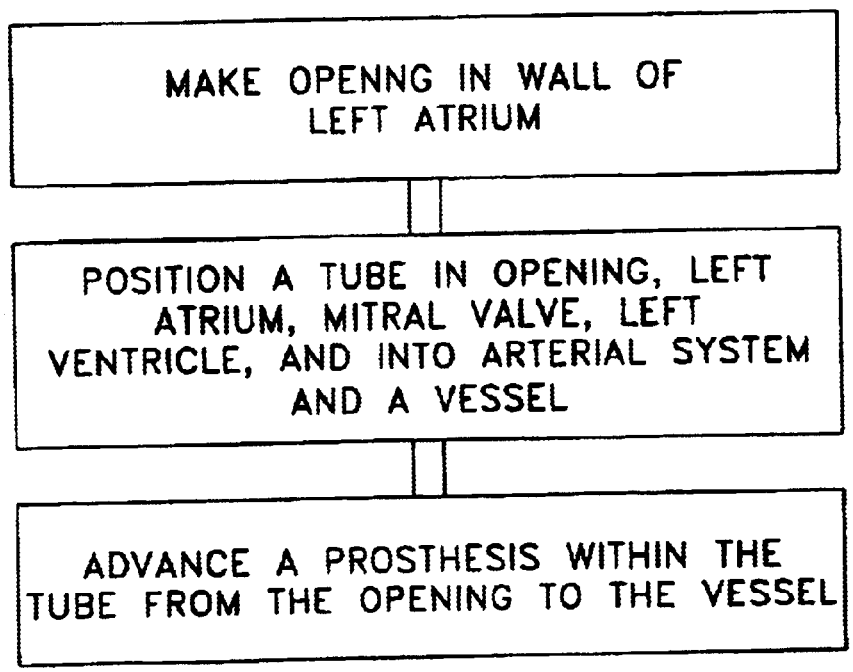
FIG. 16 is a block diagram flow chart illustrating the method shown pictorially in FIG. 15.

Thus, for example, in an alternative preferred embodiment, a wire, a catheter, a tube 900 (FIG. 15) or any other filament can be placed from the left atrium 5, through the ventricle 25 and into the arterial system 20, over (or through) which a prosthesis or device can be advanced (pushed or pulled). As an example, a catheter with a balloon can be placed through an incision in the left atrial wall. The balloon can be inflated and this catheter can then be "floated" along the flow of blood across the mitral valve, into the left ventricle, and out into the arterial system. At that point the catheter can be grasped by an instrument placed through a small incision in the aorta or passed into the aorta by means of a remote vessel such as the femoral artery. At this point, the prosthesis or device can be mounted onto the catheter and either be pushed (or pulled) over the catheter into position. This procedure can be similarly performed by the use of a wire or other filament structure. Also, a tube could be employed, with the prosthesis or device being advanced within the tube.

Figure 12:
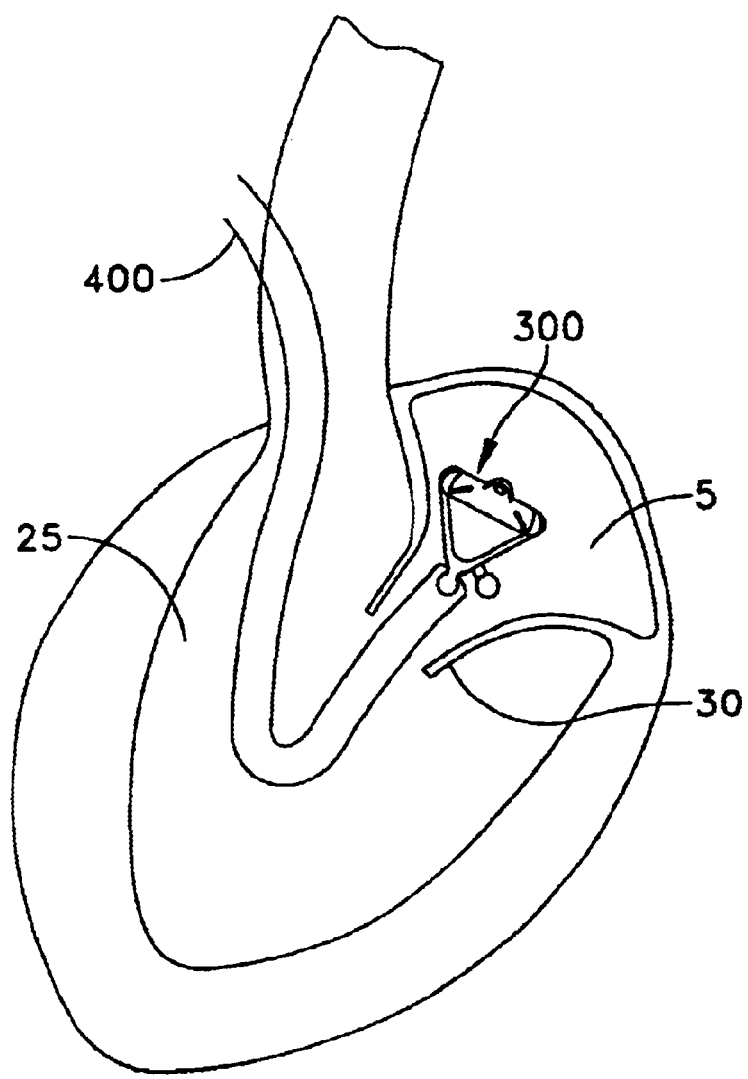
FIG. 12 is similar to FIG. 1, but illustrative of an alternative approach of the first manipulation instrument.
Figure 13:
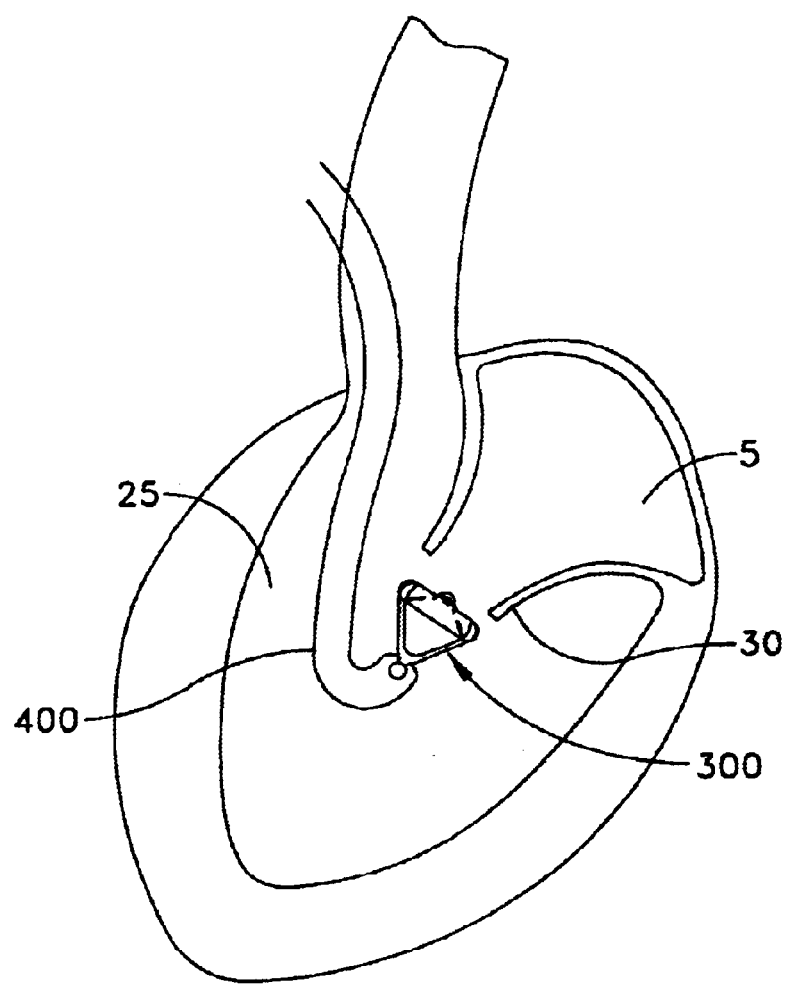
FIG. 13 is similar to FIG. 2, but illustrative of the alternative approach of FIG. 12.
Figure 14:
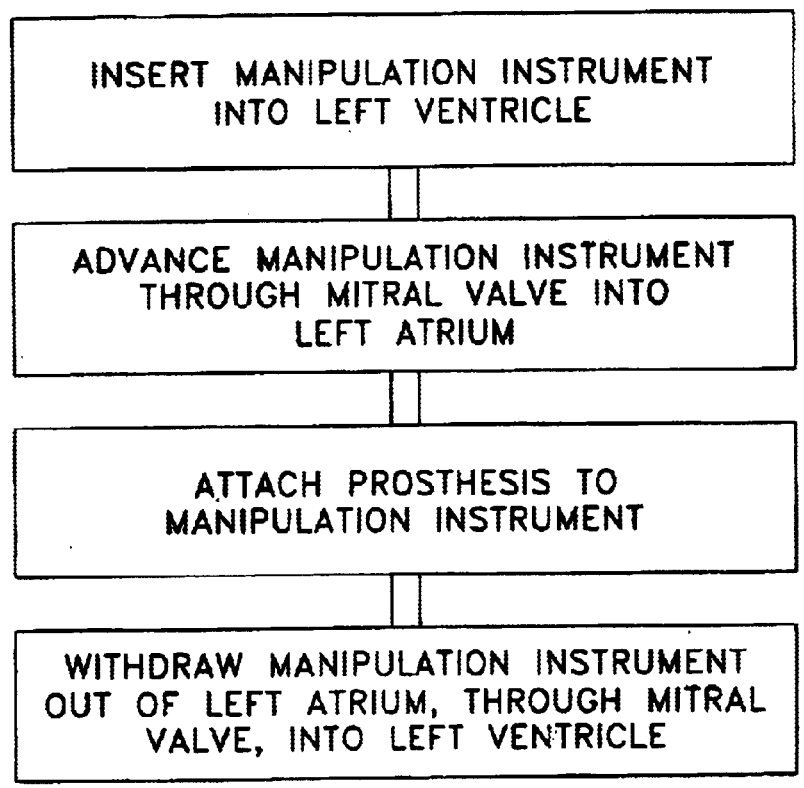
FIG. 14 is a black diagram flow chart of the method pictorially illustrated in FIGS. 12 and 13.

In a further alternative embodiment (FIG. 14), the method for inserting a prosthesis or device into a vessel within the arterial system can be accomplished by inserting the manipulation instrument 400 into the left ventricle 25, advancing the manipulation instrument through the mitral valve 30 and into the left atrium 5, attaching the prosthesis or device assembly onto the manipulation instrument 400 (FIG. 12), and withdrawing the manipulation instrument 400 out of the left atrium 5, across the mitral valve 30, and into the left ventricle 25 (FIG. 13).

What is claimed is:

1. A method of inserting a prosthesis or device into a vessel within the arterial system comprising the steps of:
    making an opening in a wall of a low pressure region of the heart;
    advancing a first manipulation instrument to advance the prosthesis or device through the opening and into the low pressure region and
    through a natural barrier between the low pressure region and the left ventricle; and
    advancing a second manipulation instrument to transfer the prosthesis or device from the first instrument to the second instrument and to advance the prosthesis or device from the left ventricle into the arterial system and the vessel.

2. The method of claim 1 wherein the natural barrier comprises the mitral valve.

3. The method of claim 1 wherein the wall is the external wall of the left atrium, and the natural barrier is the mitral valve.

4. A method of inserting a prosthesis or device into a vessel within the arterial system comprising the use of first and second manipulation instruments for advancing the prosthesis or device and the steps of:
    making an opening in a wall of the left atrium;
    advancing the first manipulation instrument to advance the prosthesis or device through the opening, into the left atrium, through the mitral valve and into the left ventricle; and
    advancing the second manipulation instrument through a second incision into the arterial system and into the left ventricle, to advance the prosthesis or device from the left ventricle into the arterial system and the vessel.

5. The method of claim 4 wherein the prosthesis or device is an aortic valve prosthesis.

6. The method of claim 4 wherein the vessel is the aorta.

7. The method of claim 4 wherein the prosthesis or device is releasably attached to a prosthesis holding apparatus carried by the first manipulation instrument as the prosthesis or device is advanced through the left atrium and the mitral valve to the left ventricle.

8. The method of claim 7 wherein the prosthesis holding apparatus and the attached prosthesis are advanced by means of the first manipulation instrument to which the prosthesis holding apparatus is releasably attached.

9. A method for inserting a prosthesis or device into a vessel within the arterial system comprising the steps of:
    inserting a manipulation instrument into the left ventricle;
    advancing the manipulation instrument through the mitral valve and into the left atrium;
    attaching the prosthesis or device onto the manipulation instrument; and
    withdrawing the manipulation instrument out of the left atrium, across the mitral valve and into the left ventricle.

10. A method of inserting a prosthesis or device from a lower pressure region into a higher pressure region of an arterial system, and to a vessel thereof comprising the steps of:
    making an opening in a wall of a left atrium,
    advancing the prosthesis or device through the opening and into the left atrium; and
    advancing the prosthesis or device through a natural barrier between the left atrium and a left ventricle;
    wherein a tube is first positioned in the left atrium, advanced across the mitral valve, and advanced across the left ventricle and into the arterial system and the vessel, and further wherein the prosthesis or device is then advanced within the tube from the opening in the left atrium to the vessel.

11. A method of mounting a prosthesis or device in a vessel within an arterial system, the method comprising the steps of:
    advancing a first manipulation instrument to advance the prosthesis or device into a low pressure region of the system and through a natural barrier between the low pressure region and a high pressure region;
    advancing a second manipulation instrument into the high pressure region to engage and connect to the prosthesis or device while the prosthesis or device is connected to the first manipulation instrument; and further advancing the second manipulation instrument to advance the prosthesis or device to a selected destination in the arterial system.

12. The method of claim 11 wherein the prosthesis or device is simultaneously held by the first manipulation instrument and the second manipulation instrument.

13. A method of mounting a prosthesis or device in a vessel within an arterial system, the method comprising the steps of:
   advancing a first manipulation instrument to advance the prosthesis or device into a low pressure region of the system and through a natural barrier between the low pressure region and a high pressure region;
   advancing a second manipulation instrument into the high pressure region to engage and connect to the prosthesis or device while the prosthesis or device is connected to the first manipulation instrument; and
   disconnecting the first manipulation instrument from the prosthesis or device, leaving the prosthesis or device connected to the second manipulation instrument; and
   further advancing the second manipulation instrument to advance the prosthesis or device to a selected destination in the arterial system.

14. A method of inserting a prosthesis or device disposed in the left atrium into a vessel within the arterial system, the method comprising the use of first and second manipulation instruments for advancing the prosthesis or device, and further comprising the steps of:
   advancing the first manipulation instrument to advance the prosthesis or device through the mitral valve and into the left ventricle; and
   advancing the second manipulation instrument into the arterial system and into the left ventricle to engage the prosthesis or device and advance the prosthesis or device from the left ventricle into the arterial system and into the vessel.

15. A method of inserting a prosthesis or device into a vessel within the arterial system comprising the steps of:
   advancing the prosthesis or device through the mitral valve and into the left ventricle;
   advancing the prosthesis or device from the left ventricle into the arterial system and the vessel;
   further comprising the use of first and second manipulation instruments for advancing the prosthesis or device, wherein:
   the first manipulation instrument is used to advance the prosthesis or device into the left atrium, through the mitral valve and into the left ventricle; and
   the second manipulation instrument, passing through a second incision into the arterial system and advanced into the left ventricle, is used to advance the prosthesis or device from the left ventricle into the arterial system and the vessel.

* * * * *